United States Patent
Christensen et al.

(10) Patent No.: US 11,793,407 B2
(45) Date of Patent: *Oct. 24, 2023

(54) DETERMINING BIOMETRIC DATA USING AN ARRAY OF INFRARED ILLUMINATORS

(71) Applicant: Micron Technology, Inc., Boise, ID (US)

(72) Inventors: Carla L. Christensen, Boise, ID (US); Bhumika Chhabra, Boise, ID (US); Zahra Hosseinimakarem, Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/100,097

(22) Filed: Jan. 23, 2023

(65) Prior Publication Data

US 2023/0148866 A1    May 18, 2023

Related U.S. Application Data

(63) Continuation of application No. 17/569,746, filed on Jan. 6, 2022, now Pat. No. 11,559,206, which is a continuation of application No. 17/092,678, filed on Nov. 9, 2020, now Pat. No. 11,219,371.

(51) Int. Cl.
| | |
|---|---|
| *A61B 5/00* | (2006.01) |
| *A61B 5/01* | (2006.01) |
| *A61B 5/024* | (2006.01) |
| *G06V 10/141* | (2022.01) |
| *G06V 10/143* | (2022.01) |
| *G06V 40/70* | (2022.01) |
| *G06V 40/10* | (2022.01) |

(52) U.S. Cl.
CPC .......... *A61B 5/0082* (2013.01); *A61B 5/0015* (2013.01); *A61B 5/015* (2013.01); *A61B 5/02433* (2013.01); *G06V 10/141* (2022.01); *G06V 10/143* (2022.01); *G06V 40/70* (2022.01); *G06V 40/15* (2022.01)

(58) Field of Classification Search
CPC ..... A61B 5/0082; A61B 5/0015; A61B 5/015; A61B 5/02433; G06V 10/141; G06V 10/143
See application file for complete search history.

(56) References Cited

U.S. PATENT DOCUMENTS

| | | |
|---|---|---|
| 7,340,293 B2 | 3/2008 | McQuilkin |
| 7,627,147 B2 | 12/2009 | Loiacono et al. |
| 8,463,006 B2 | 6/2013 | Prokoski |
| 9,836,648 B2 | 12/2017 | Perna et al. |
| 10,628,729 B2 | 4/2020 | Sareen |
| 2019/0192010 A1 | 6/2019 | Mane |

(Continued)

*Primary Examiner* — Casey L Kretzer
(74) *Attorney, Agent, or Firm* — Brooks, Cameron & Huebsch, PLLC (57) ABSTRACT

Methods, devices, and systems related to determining biometric data using an array of infrared (IR) illuminators are described. In an example, a method can include projecting a number of IR dots on a user using a dot projector and an array of IR illuminators, capturing an IR image of the number of IR dots using an IR camera, comparing a number of pixels of the captured IR image to a number of corresponding pixels of a baseline IR image using a processing resource, and determining biometric data of the user at least partially based on comparing the captured IR image to the baseline IR image using the processing resource.

20 Claims, 3 Drawing Sheets

(56) References Cited

U.S. PATENT DOCUMENTS

| | | |
|---|---|---|
| 2021/0038144 A1 | 2/2021 | Watanabe |
| 2021/0064855 A1* | 3/2021 | Wang .................. G06V 10/143 |
| 2021/0218589 A1 | 7/2021 | Shimizu |
| 2023/0111692 A1* | 4/2023 | Sultanbekov ........ G06V 40/174 |
| | | 348/77 |

* cited by examiner

DETERMINING BIOMETRIC DATA USING AN ARRAY OF INFRARED ILLUMINATORS

PRIORITY INFORMATION

This application is a Continuation of U.S. application Ser. No. 17/569,746, filed on Jan. 6, 2022, which is a Continuation of U.S. application Ser. No. 17/092,678, filed on Nov. 9, 2020, which issued as a U.S. Pat. No. 11,219,371 on Jan. 11, 2022, the contents of which are incorporated herein by reference.

TECHNICAL FIELD

The present disclosure relates generally to an array of infrared (IR) illuminators, and more particularly, to methods, apparatuses, and systems related to determining biometric data of a user using an array of IR illuminators.

BACKGROUND

An IR illuminator can be, for example, a device that emits IR light. IR is a region of the electromagnetic radiation spectrum. Wavelengths in the IR region range from about 700 nanometers (NM) to 1 millimeter (mm). A dot projector can project IR light as a grid pattern. An IR camera, also known as a thermographic camera or thermal imaging camera, can capture IR light and form a heat zone image using the IR light.

DETAILED DESCRIPTION

The present disclosure includes methods, apparatuses, and systems related to determining biometric data using an array of IR illuminators. An example method includes projecting a number of IR dots on a user using a dot projector and an array of IR illuminators, capturing an IR image of the number of IR dots using an IR camera, comparing a number of pixels of the captured IR image to a number of corresponding pixels of a baseline IR image using a processing resource, and determining biometric data of the user at least partially based on comparing the captured IR image to the baseline IR image using the processing resource. The determined biometric data can include a user's heart rate, temperature, calorie burn rate (e.g., number of calories burned over a period of time), physical state, and/or emotional state. The user's health (e.g., physical state) can be determined based on a heat distribution (e.g., intensity parameter per pixel) in the IR image of the user's face and the user's athletic state (e.g., physical state) can be determined based on a heat distribution in the IR image of the user's muscles. For example, a muscle being exercised will generate more heat than a muscle not being exercised. In some examples, the user's emotional state can be at least partially determined based on a user's posture, facial expression, sounds, and/or gestures.

As used herein, a user can be one or more users. The IR image of the user can include an entire body of a user or a portion of the body of the user. A portion of the body of the user can be a face, head, eye, ear, nose, leg, arm, or hand, for example.

The baseline IR image can also include an entire body or a portion of a body. The baseline IR image can be a neutral condition of the user, an average IR image of the user created by a number of previously taken IR images of the user, or an IR image of an average person from a library, for example.

A single IR illuminator can emit IR light over an area and an array of IR illuminators (e.g., a plurality of IR illuminators) can emit IR light over a greater area. For example, where a single IR illuminator could emit IR light over a user's face, an array of IR illuminators could emit IR light over a user's entire body. Covering a user's entire body with IR light can allow the IR camera to capture an IR image of the user's entire body.

In a number of embodiments, a first portion of the number of IR dots can be projected by the dot projector on a first portion of a user's body and a second portion of the number of IR dots can be projected by the dot projector on a second portion of the user's body. In some examples, the first portion of the number of IR dots can be a first diameter and the second portion of the number of IR dots can be a second diameter. A dot diameter can be smaller when a dot is being projected on to a portion of the user's body where more detail in the IR image is desired and a dot diameter can be larger when a dot is being projected on to a portion of the user's body where less detail in the IR image is desired. The dot projector may project dots with smaller diameters on to a portion of the user's body where the user's body has more changes in contour, color, and/or shape. For example, the dot projector may project dots with smaller diameters on to a user's face and project dots with larger diameters on to a user's torso. In some examples, decreasing an IR dot diameter allows more dots to be projected in an area, which creates a more detailed IR image of the user in that area.

As such, the number of IR dots the dot projector projects on a portion of a user's body can be dependent on where more detail in the IR image is desired. The dot projector can project a first portion of the number of the IR dots on a first portion of the user's body and project a second portion of the number of the IR dots on a second portion of the user's body, where the first portion of the number of the IR dots is greater than the second portion of the number of IR dots. The dot projector may project a greater number of the IR dots on a portion of the user's body where the user's body has more changes in contour, color, and/or shape. For example, the dot projector may project a greater number of IR dots on to an ear of the user than on to a chin of the user because the user's ear has more contours than the user's chin.

In a number of embodiments, an axicon or an array of axicons can be used in conjunction with an array of IR illuminators, a dot projector, and/or an IR camera. An axicon is a cone shaped optical element with a circular aperture. The axicon can prevent light diffraction. An IR light can diffract and lose its intensity with distance. Placing an axicon in front of the dot projector will make the IR light diffraction free and allow the IR light to maintain its intensity over a greater distance. In some examples, an apparatus including an array of IR illuminators, a dot projector, an array of axicons, and an IR camera can project and capture an IR image of a number of IR dots at a greater distance away from the apparatus than an apparatus including the array of IR illuminators, the dot projection, and the IR camera without the array of axicons.

The IR camera can capture the IR light emitted by the array of IR illuminators and form an IR image (e.g., a heat zone image) using the number of IR dots. In a number of embodiments, a number of IR cameras can be used to capture a number of IR images. For example, each of the number of IR cameras can be located at different locations to capture IR images of the user on different sides of the user and/or different angles of the user.

As used herein, "a number of" something can refer to one or more of such things. For example, a number of computing devices can refer to one or more computing devices. A "plurality" of something intends two or more. Additionally, designators such as "X" and "Y", as used herein, particularly with respect to reference numerals in the drawings, indicates that a number of the particular feature so designated can be included with a number of embodiments of the present disclosure.

The figures herein follow a numbering convention in which the first digit or digits correspond to the drawing figure number and the remaining digits identify an element or component in the drawing. Similar elements or components between different figures may be identified by the use of similar digits. For example, reference numeral 102 may reference element "2" in FIG. 1, and a similar element may be referenced as 202 in FIG. 2. In some instances, a plurality of similar, but functionally and/or structurally distinguishable, elements or components in the same figure or in different figures may be referenced sequentially with the same element number (e.g., 104-1, 104-2, and 104-X in FIG. 1). As will be appreciated, elements shown in the various embodiments herein can be added, exchanged, and/or eliminated so as to provide a number of additional embodiments of the present disclosure. In addition, the proportion and the relative scale of the elements provided in the figures are intended to illustrate various embodiments of the present disclosure and are not to be used in a limiting sense.

Figure 1:
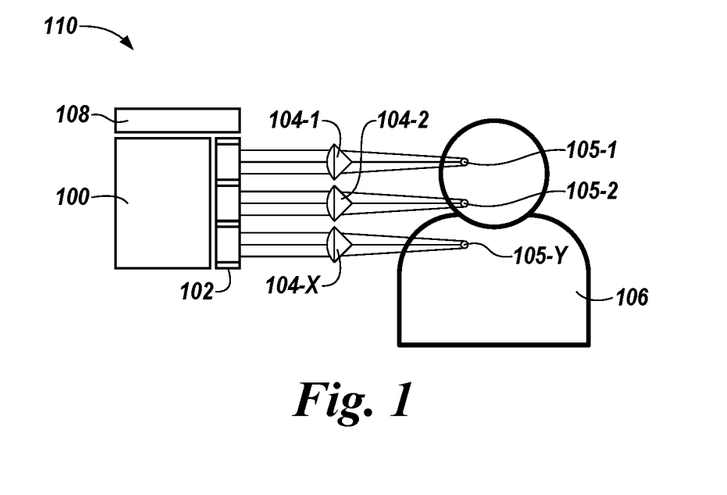
FIG. 1 illustrates an example of an apparatus for determining biometric data of a user in accordance with a number of embodiments of the present disclosure.

FIG. 1 illustrates an example of an apparatus 110 for determining biometric data of a user 106 in accordance with a number of embodiments of the present disclosure. The apparatus 110 can be, but is not limited to, a television, a smart television, a gaming system, a piece of fitness equipment, a smart mirror, a computing device, a personal laptop computer, a desktop computer, a smart phone, a tablet, a wrist worn device, a digital camera, and/or redundant combinations thereof. The apparatus 110, as illustrated in FIG. 1, can include an infrared illuminator 100, a dot projector 102, a number of axicons 104-1, 104-2, . . . , 104-X, and an IR camera 108.

Biometric data can include a user's heart rate, temperature, calorie burn rate, physical state, and/or emotional state, for example. The user's emotional state can be at least partially determined based on a user's posture, facial expression, sounds, and/or gestures.

One or more of the IR images can be used to determine a user's heart rate, temperature, calorie burn rate, posture, facial expression, and/or gestures. The one or more IR images can be created by projecting a number of IR dots 105-1, 105-2, . . . , 105-Y on a user 106 using a dot projector 102 and an IR illuminator 100 and capturing an IR image of the number of IR dots 105-1, 105-2, . . . , 105-Y using an IR camera 108.

The IR illuminator 100 can emit IR light. The IR illuminator 100 can be a single IR illuminator and/or an array of IR illuminators. As previously described, an array of IR illuminators can emit IR light over a greater area than a single IR illuminator. For example, a single IR illuminator can emit IR light over a portion of a user's body and an array of IR illuminators can emit IR light over a number of users.

The dot projector 102 utilizing the IR light emitted by the IR illuminator 100 can project the number of dots 105-1, 105-2, . . . , 105-Y directly on the user 106 and/or a number of users from the dot projector 102 and/or from the dot projector 102 through the number of axicons 104-1, 104-2, . . . , 104-X6666. For example, a first portion of the number of IR dots 105-1, 105-2, . . . , 105-Y can be projected by the dot projector 102 on a first user and a second portion of the number of IR dots 105-1, 105-2, . . . , 105-Y can be projected by the dot projector 102 on a second user.

In a number of embodiments, a first portion of the number of IR dots 105-1, 105-2, . . . , 105-Y can be projected by the dot projector 102 on a first portion of the body of the user 106 and a second portion of the number of IR dots 105-1, 105-2, . . . , 105-Y can be projected by the dot projector 102 on a second portion of the body of the user 106. For example, the first portion of the number of IR dots 105-1, 105-2, . . . , 105-Y can include IR dots 105-1 and 105-2 and the second portion of the number of IR dots 105-1, 105-2, . . . , 105-Y can include IR dot 105-Y.

The first portion of the number of IR dots 105-1, 105-2, . . . , 105-Y can be a first diameter and the second portion of the number of IR dots 105-1, 105-2, . . . , 105-Y can be a second diameter. In some examples, the diameter of an IR dot can be determined by the distance the IR light is traveling from the IR projector 102. For example, the farther the IR light travels, the larger the IR dot will be, as such, the IR projector 102 can project a smaller IR dot when a user 106 is farther away and a larger IR dot when the user 106 is closer to the IR projector 102.

Although not shown in FIG. 1, an IR dot diameter can be smaller when an IR dot is being projected on to a portion of the user's body where more detail in the IR image is desired and an IR dot diameter can be larger when an IR dot is being projected on to a portion of the user's body where less detail in the IR image is desired. The dot projector 102 may project dots with smaller diameters on to a portion of the user's body where the user's body has more changes in contour, color, and/or shape. For example, the dot projector 102 may project IR dots with a smaller diameter on to a user's face and project IR dots with a larger diameter on to a user's body (e.g., neck, shoulders, chest, torso, arms, and/or legs, etc.). In some examples, decreasing an IR dot diameter allows more IR dots to be projected in an area, which creates a more detailed IR image of the user 106 in that area.

The number of IR dots 105-1, 105-2, . . . , 105-Y the dot projector 102 projects on a portion of a user's body can be dependent on where more detail in the IR image is desired. The dot projector 102 can project a first portion of the number of the IR dots 105-1, 105-2, . . . , 105-Y on a first portion of the user's body and project a second portion of the number of the IR dots 105-1, 105-2, . . . , 105-Y on a second portion of the user's body. The dot projector 102 may project a greater number of the IR dots 105-1, 105-2, . . . , 105-Y on a portion of the user's body where the user's body has more changes in contour, color, and/or shape. For example, the dot projector 102 may project a greater number of the IR dots 105-1, 105-2, . . . , 105-Y on to an ear of the user 106 than on to a chin of the user 106 because the user's ear has more contours than the user's chin.

In a number of embodiments, an axicon 104 or an array of axicons 104-1, 104-2, . . . , 104-X can be used in conjunction with an IR illuminator 100, dot projector 102, and/or IR camera 108. An axicon 104 is a cone shaped optical element with a circular aperture. The axicon 104 can prevent light diffraction. An IR light can diffract and lose its intensity with distance. Placing an axicon 104 in front of the dot projector 102 will make the IR light diffraction free and allow the IR light to maintain its intensity over a greater distance. In some examples, an apparatus 110 including an IR illuminator 100, a dot projector 102, an array of axicons 104-1, 104-2, . . . , 104-X, and an IR camera 108 can project and capture an image of a number of IR dots 105-1, 105-2, . . . , 105-Y at a greater distance away from the apparatus 110 than an apparatus without the array of axicons 104-1, 104-2, . . . , 104-X.

The IR camera 108 can capture the IR light emitted by the IR illuminator 100 and capture an IR image of the number of IR dots 105-1, 105-2, . . . , 105-Y. In a number of embodiments, a number of IR cameras 108 can be used to capture the number of IR dots 105-1, 105-2, . . . , 105-Y. For example, each of the number of IR cameras 108 can be located at different locations to capture the number of IR dots 105-1, 105-2, . . . , 105-Y on different sides of the user 106.

Figure 2:
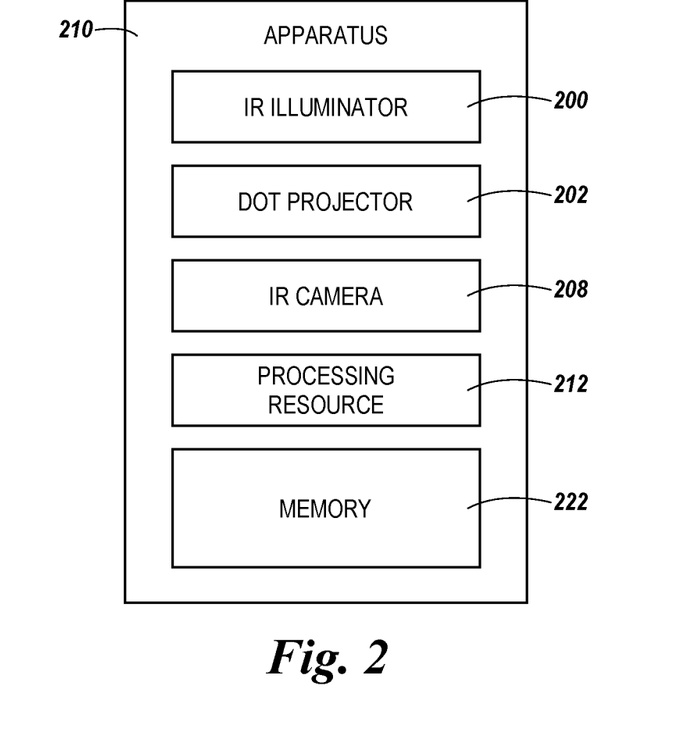
FIG. 2 illustrates an example of an apparatus for determining biometric data of a user in accordance with a number of embodiments of the present disclosure.

FIG. 2 illustrates an example of an apparatus 210 for determining biometric data of a user in accordance with a number of embodiments of the present disclosure. Apparatus 210 can correspond to apparatus 110 in FIG. 1. The apparatus 210 can include an infrared illuminator 200, a dot projector 202, and an IR camera 208. The infrared illuminator 200, the dot projector 202, and the IR camera 208 can correspond to the infrared illuminator 100, the dot projector 102, and the IR camera 108, respectively in FIG. 1. As illustrated in FIG. 2, apparatus 210 can further include a processing resource 212 and a memory 222.

The memory 222 can be any type of storage medium that can be accessed by the processing resource 212 to perform various examples of the present disclosure. For example, the memory 222 can be a non-transitory computer readable medium having computer readable instructions (e.g., computer program instructions) stored thereon that are executable by the processing resource 212 to produce an IR light via an IR illuminator, project a number of IR dots on a user via the dot projector using the IR light produced by the IR illuminator, capture an IR image of the number of IR dots via an IR camera, compare a number of pixels of the captured IR image to a number of corresponding pixels of a baseline IR image, and determine biometric data of the user at least partially based on comparing the captured IR image to the baseline IR image.

In a number of embodiments, one or more sensors, not illustrated in FIG. 2, can be included in the apparatus 210. For example, the apparatus 210 can include a visible light camera to capture a visible light image. A captured visible light image can be used with the captured IR image to determine biometric data of a user. For example, a captured visible light image can include a facial expression that can be used to determine an emotional state of a user. However, facial expressions may mean different emotional states based on a person's geographical location, race, and/or culture. Accordingly, a captured IR image can be used in conjunction with a captured visible light image to determine a true emotional state of a user.

The processing resource 212 can receive the one or more IR images from the IR camera 208 and/or from memory 222. In some examples, the processing resource 212 can combine an IR image from the IR camera 208 with an IR image from the memory 222. For example, the IR image from the IR camera 208 can be less detailed than the IR image from memory 222 because it was captured from a greater distance away from the user than the IR image from the memory 222. The processing device 212 can use the IR image from the memory 222 with the IR image from the IR camera 208 to create more accurate biometric data of the user.

In a number of embodiments, the memory 222 can store biometric data of the user. In some examples, the biometric data can be used when playing video games, watching a movie, watching instructional videos, and/or fitness videos.

The memory 222 can be volatile or nonvolatile memory. The memory 222 can also be removable (e.g., portable) memory, or non-removable (e.g., internal) memory. For example, the memory 222 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disc read-only memory (CD-ROM)), flash memory, a laser disc, a digital versatile disc (DVD) or other optical storage, and/or a magnetic medium such as magnetic cassettes, tapes, or disks, among other types of memory.

Further, although memory 222 is illustrated as being located within apparatus 200, embodiments of the present disclosure are not so limited. For example, memory 222 can be located on an external apparatus (e.g., enabling computer readable instructions to be downloaded over the Internet or another wired or wireless connection).

Figure 3:
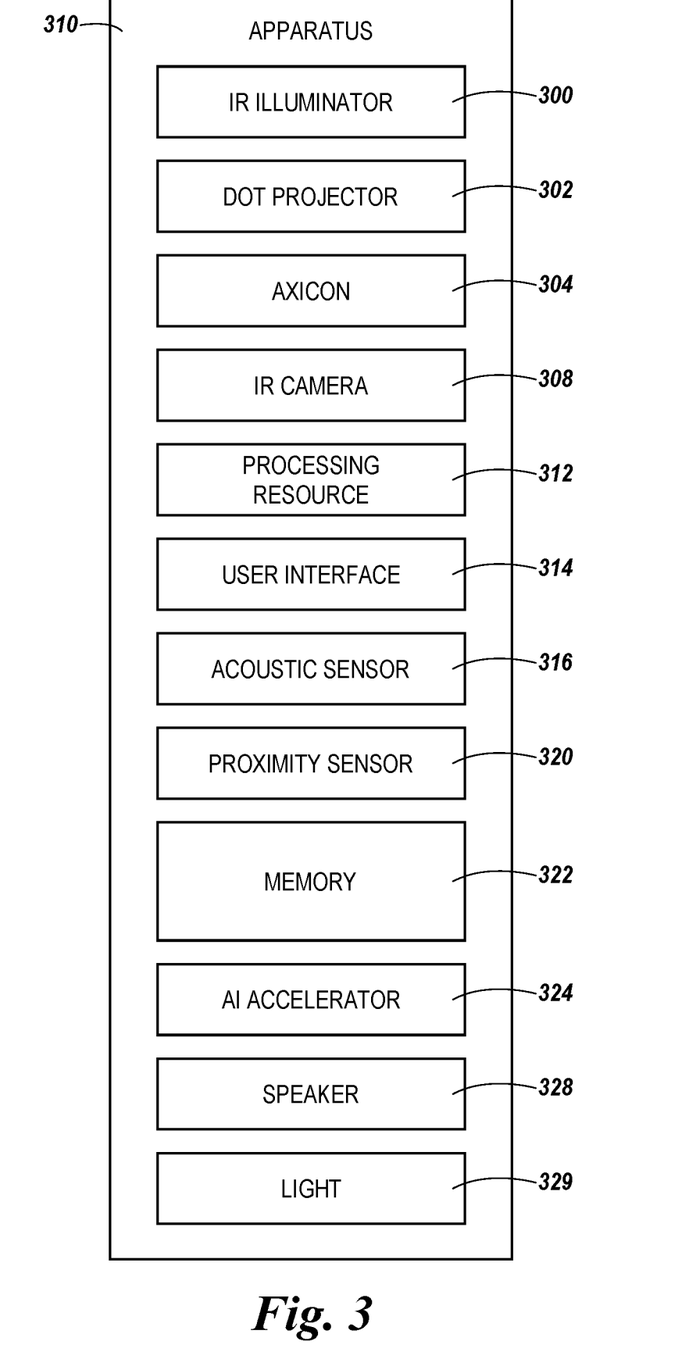
FIG. 3 illustrates an example of an apparatus for determining biometric data of a user in accordance with a number of embodiments of the present disclosure.

FIG. 3 illustrates an example of an apparatus 310 for determining biometric data of a user in accordance with a number of embodiments of the present disclosure. Apparatus 310 can correspond to apparatus 210 in FIG. 2. The apparatus 310 can include an IR illuminator 300, a dot projector 302, an axicon 304, an IR camera 308, a processing resource 312, and a memory 322. The IR illuminator 300, the dot projector 302, the IR camera 308, the processing resource 312, and the memory 322 can correspond to the infrared illuminator 200, the dot projector 202, the IR camera 208, the processing resource 212, and the memory 222, respectively in FIG. 2. The axicon 304 can correspond to the axicon 104 in FIG. 1. As illustrated in FIG. 3, apparatus 310 can further include a user interface 314, an acoustic sensor 316, a proximity sensor 320, an AI accelerator 324, a speaker 328, and a light 329.

An AI accelerator 324 can include hardware, software, and/or firmware that is configured to perform operations (e.g., logic operations, among other operations) associated with AI operations using one or more AI models. An AI model can be stored in memory 322 and/or external to the apparatus 310. In a number of embodiments, an AI model can be trained on and/or external to the apparatus 310. Data from a user or sample data can be used to train an AI model. In some examples, a number of heart rates, heart rate conditions (e.g., frequency and/or amplitude of a heart beat), temperatures, calorie burn rates, physical states and/or emotional states of a person with corresponding baseline IR images can be used to train an AI model. For example, a baseline IR image identified as a person with an angry emotional state can be used to train an AI model. The baseline IR image of an angry person will include more heat generated by blood flow than an IR image of a relaxed person. For example, the baseline IR image of an angry person will include a number of pixels within a particular color value range.

The AI accelerator 324 can include train parameters to train the AI model. Train parameters can include intensity and luminance distribution, intensity or heat profile at different wavelengths (e.g., spectra), spatial distribution comparison on high-pass and/or low-pass filtered data, a difference between two IR images in Fourier domain, and/or feature extraction and classification.

Data from a captured IR image can be inputted into an AI model. The data can include color values of each pixel of the captured IR image. The color values of each of the number of pixels can be compared to color values of each of a number of pixels from one or more baseline IR images. For example, the AI model can compare a number of pixels of a captured IR image to a number of corresponding pixels of a baseline IR image. The number of pixels of the captured IR image can correspond to the number of pixels of the baseline IR image if the number of pixels of the captured image and the number of pixels of the baseline IR image are from the same particular area of a face, for example. If the number of pixels of the captured IR image are within a particular color value range of the number of pixels of the baseline image then biometric data of a user (e.g., a heart rate, temperature, calorie burn rate, physical state, and/or emotional state) may be the same or similar to the biometric data identified with the baseline IR image.

In some examples, biometric data of a user in a captured IR image can be determined by extrapolating biometric data of a baseline IR image. For example, a baseline IR image can be associated with a temperature. The temperature associated with the captured IR image can be determined by comparing the captured IR image to the baseline IR image to determine a difference value and using the difference value and the temperature associated with the baseline IR image to calculate the temperature associated with the captured IR image. The user interface 314 can be generated by the apparatus 310. The user interface 314 can be a graphical user interface (GUI) that can provide and/or receive information to and/or from the user of the apparatus 310. The user interface 314 can be shown on a display of the apparatus 310.

In a number of embodiments, the user interface 314 can be generated in response to an input from a user. A user input to generate the user interface 314 can include powering on the apparatus 310 and/or selecting an application, for example.

Once the user interface 314 is generated on the apparatus 310, the user interface 314 can display a video. In some examples, the video can be a video game, a movie, an instructional video, or a fitness video. In a number of embodiments, AI operations can be performed on the biometric data using an AI accelerator 324 and the video can be modified in response to the output of the AI operation.

The video can be modified in response to biometric data of the user. For example, the AI accelerator 324 can output a command to slow down, speed up, and/or shutoff the video in response to performing an AI operation on the biometric data of the user. In a number of embodiments, the video can be slowed down or sped up in response to the determined biometric data of the user being outside of a particular range. The particular range can be a healthy heartrate range, for example, if the user's heartrate is below the particular range the video can be sped up and if the user's heartrate is above a particular range the video can be slowed down. An IR image can capture the size of a vein and over a number of IR images track the vein getting larger and smaller to determine the heartrate of the user.

The AI accelerator 324 could determine that the user is getting bored of a video game by analyzing the one or more captured IR images and speed up the video game. The AI accelerator 324 could determine that the user was getting bored by quantifying the rate at which the user looks away from the user interface 314. For example, the AI accelerator 324 can determine, using a first number of IR images over a first period of time, that the user looks away from the user interface 314 a first number of times and determine, using a second number of IR images over a second period of time, that the user looks away from the user interface 314 a second number of times. If the second number of times the user looks away from the user interface 314 is greater than the first number of times, the AI accelerator 324 can output a command to speed up the game to try to reengage the user with the video game.

In some examples, the story, quest, and/or goal of the video can be changed in response to the biometric data of the user. For example, the processing resource 312 can determine that the user has reached their heartrate goal by calculating the user's heartrate using a number of IR images over a period of time. In response to the user meeting their heartrate goal, the AI accelerator 324 can create a new fitness goal for the workout video.

The user interface 314 can also display messages. Messages can be displayed in response to outputs of an AI operation. For example, the AI accelerator 324 can determine that the user's heart rate is irregular, and the user is in need of medical attention. In response to the AI operation determining the user is in need of medical attention, a message that the user is in need of medical attention can be displayed on the user interface 314.

The apparatus 310 can include an acoustic sensor 316. The acoustic sensor 316 can detect sounds produced by a user. Detected sounds can include, but are not limited to, speaking, breathing, and/or footsteps, for example. The language, volume, and/or pitch of the sound captured by the acoustic sensor 316 can be analyzed by the AI accelerator 324. In a number of embodiments, AI operations can be performed on the sound data using the AI accelerator 324. For example, the AI accelerator 324 can determine that the user is exhausted by performing an AI operation on the sound data. The sound data can include a recording of the breathing of the user over a period of time. In response to the AI accelerator 324 determining that the user is breathing faster over the period of time, the AI accelerator 324 can output a command to slow down the video and/or change the goal of the video, for example.

A movement of the user can be detected using the proximity sensor 320. An AI operation can be performed on the data collected by the proximity sensor 320 from the user's movement. The AI accelerator 324 can determine a speed of the user's movement, the force of the user's movement, and/or the direction of the user's movement. In some examples, the AI accelerator 324 can determine an outcome of a story, quest, and/or goal based on the determined speed, the determined force, and/or the determined direction of the user's movement. For example, a user's swing may have been in the right direction and had enough force to sink a putt and move the user on to a new hole in a golf video game.

A speaker 328 can be included in apparatus 310. The speaker 328 can produce a sound and/or sounds based on an output of an AI operation. For example, the AI accelerator 324 can perform an AI operation on biometric data of the user and determine a physical and/or an emotional state of the user. The biometric data can include an IR image of the user with a slouched posture and/or a frowning facial expression. Based on the IR image, the AI accelerator 324 can determine that the user is sad. In response to the AI accelerator 324 determining that the user is sad, the speaker 328 can play an upbeat song and/or play the user's favorite song, for example.

The apparatus 310 can include a light 329. Similar, to the speaker 328, the light 329 can emit a type of light based on an output of the AI operation. For example, the AI accelerator 324 can perform an AI operation on biometric data of the user and determine a physical and/or an emotional state of the user. The biometric data can include a number of IR images with the user's eyes closed. Based on the number of IR images, the AI accelerator 324 can determine that the user is sleeping. In response to the AI accelerator 324 determining that the user is sleeping, the light 329 can emit a soft night light glow.

Figure 4:
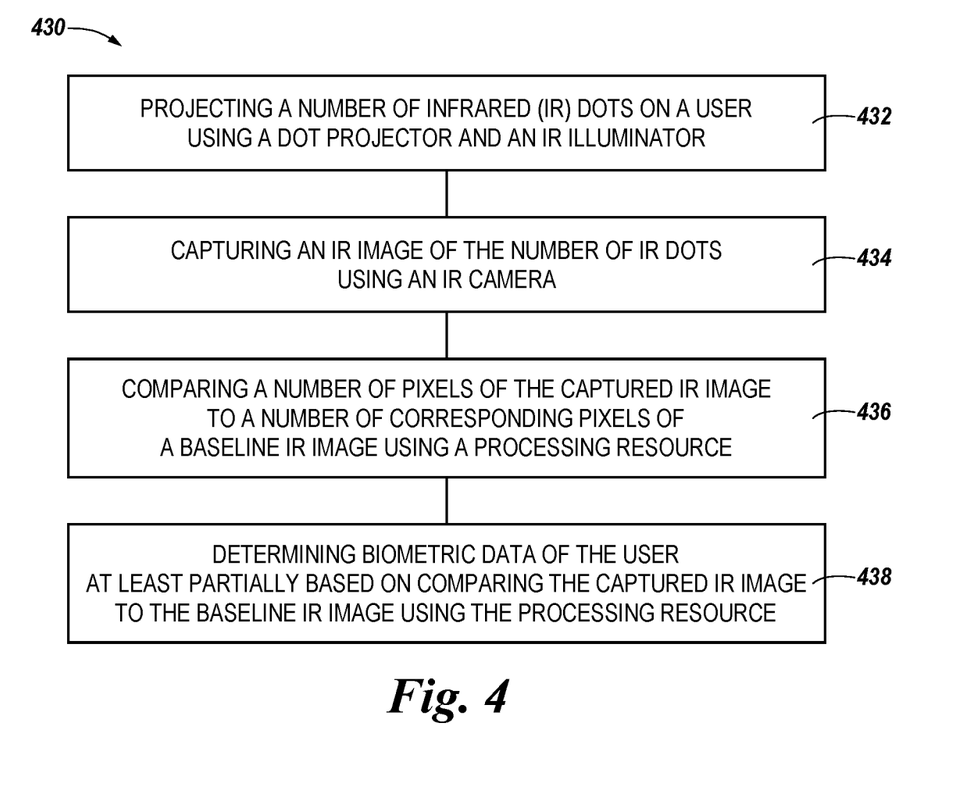
FIG. 4 is a flow diagram of a method for determining biometric data of a user in accordance with a number of embodiments of the present disclosure.

FIG. 4 is a flow diagram of a method 430 for determining biometric data of a user in accordance with a number of embodiments of the present disclosure. At block 432, the method 430 can include projecting a number of IR dots on a user using a dot projector and an array of IR illuminators.

The IR illuminator can emit IR light. In some examples, the IR illuminator can emit varying intensities of IR light. The dot projector can utilize the IR light emitted by the IR illuminator to project the number of dots on the user and/or a number of users. The dot projector can project the number of dots in varying sizes. In some examples, the dot projector can change the number of dots projected.

At block 434, the method 430 can include capturing an IR image of the number of IR dots using an IR camera. The IR camera can capture the IR light emitted by the IR illuminator. The IR image can be a heat zone image, for example.

At block 436, the method 430 can include comparing a number of pixels of the captured IR image to a number of corresponding pixels of a baseline IR image using a processing resource. In some examples, one or more captured IR images can be compared to one or more baseline IR images. The one or more captured IR images and/or the one or more baseline IR image can be from the IR camera and/or memory.

At block 438, the method 430 can include determining biometric data of the user at least partially based on comparing the captured IR image to the baseline IR image using the processing resource. In a number of embodiments, the biometric data can be used when playing video games, watching a movie, watching instructional videos, and/or fitness videos. For example, a video game, a movie, an instructional video, and/or a fitness video can be modified in response to biometric data.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and methods are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method, comprising:
    projecting a number of infrared (IR) dots on a user using a dot projector and an array of IR illuminators;
    capturing an IR image of the number of IR dots using an IR camera;
    comparing a number of pixels of the captured IR image to a number of corresponding pixels of a baseline IR image using a processing resource; and
    determining an emotional state of the user at least partially based on comparing the captured IR image to the baseline IR image using the processing resource.

2. The method of claim 1, further comprising determining the emotional state of the user at least partially based on a posture of the user in the captured IR image.

3. The method of claim 2, further comprising determining the emotional state of the user is sad in response to the captured IR image including the user with a slouched posture.

4. The method of claim 1, further comprising determining the emotional state of the user at least partially based on a facial expression of the user.

5. The method of claim 4, further comprising determining the emotional state of the user is sad in response to the captured IR image including the user with a frowning facial expression.

6. The method of claim 1, further comprising determining the emotional state of the user at least partially based on a gesture of the user in the captured IR image.

7. The method of claim 1, further comprising comparing a color value range of the number of pixels of the captured IR image to a color value range of the number of corresponding pixels of the baseline IR image using the processing resource.

8. The method of claim 7, further comprising determining the emotional state of the user in response to the color value range of the number of pixels of the captured IR image being within the color value range of the number of corresponding pixels of the baseline IR image using the processing resource.

9. The method of claim 8, further comprising determining the emotional state of the user is angry in response to the baseline IR image being of an angry person.

10. An apparatus, comprising:
    an array of infrared (IR) illuminators configured to produce an IR light;
    a dot projector configured to project a number of IR dots on a user using the IR light produced by the array of IR illuminators;
    an IR camera configured to capture an IR image of the number of IR dots; and a processing resource configured to:
- compare a number of pixels of the captured IR image to a number of corresponding pixels of a number of baseline IR images; and
- determine an emotional state of the user at least partially based on comparing the number of pixels of the captured IR image to the number of corresponding pixels of the number of baseline IR images.

11. The apparatus of claim 10, further comprising a visible light camera configured to capture a visible light image of the user.

12. The apparatus of claim 11, wherein the visible light image of the user includes a facial expression of the user.

13. The apparatus of claim 12, wherein the processing resource is further configured to determine the emotional state of the user based on the facial expression of the user in the visible light image.

14. An apparatus, comprising:
- an array of infrared (IR) illuminators configured to produce an IR light;
- a dot projector configured to project a number of IR dots on a user using the IR light produced by the array of IR illuminators;
- an IR camera configured to capture an IR image of the number of IR dots; and
- a processing resource configured to:
  - input data from the captured IR image into an artificial intelligence (AI) model; and
  - determine an emotional state of the user at least partially based on an output of the AI model.

15. The apparatus of claim 14, further comprising an artificial intelligence (AI) accelerator configured to perform an AI operation using the AI model.

16. The apparatus of claim 14, wherein the processing resource is configured to train the AI model on a number of emotional states using a number of baseline IR images.

17. The apparatus of claim 16, wherein the processing resource is configured to train the AI model with a baseline IR image identified as a person with an angry emotional state.

18. The apparatus of claim 17, wherein the baseline IR image of the angry person includes a number of pixels within a color value range.

19. The apparatus of claim 14, further comprising a speaker, wherein the speaker is configured to play a song in response to determining the emotional state of the user.

20. The apparatus of claim 14, further comprising a light, wherein the light is configured to emit a type of light in response to determining the emotional state of the user.

* * * * *